United States Patent
Sathaye et al.

(10) Patent No.: US 8,868,183 B2
(45) Date of Patent: Oct. 21, 2014

(54) METHOD AND APPARATUS TO IMPLEMENT MULTIPLE PARAMETER SETS IN AN IMPLANTABLE DEVICE

(75) Inventors: Alok S. Sathaye, Boston, MA (US); Shelley Cazares, Minneapolis, MN (US); Andrew P. Kramer, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1247 days.

(21) Appl. No.: 11/614,578

(22) Filed: Dec. 21, 2006

(65) Prior Publication Data

US 2008/0154323 A1    Jun. 26, 2008

(51) Int. Cl.
*A61N 1/37* (2006.01)
*A61N 1/372* (2006.01)

(52) U.S. Cl.
CPC .................................. *A61N 1/37264* (2013.01)
USPC ...................... 607/15; 607/9; 607/17; 607/27

(58) Field of Classification Search
USPC .............................. 607/15, 17, 27, 30, 32, 59
See application file for complete search history.

(56) References Cited

U.S. PATENT DOCUMENTS

| | | | |
|---|---|---|---|
| 5,487,752 A * | 1/1996 | Salo et al. ........................ | 607/17 |
| 5,509,927 A | 4/1996 | Epstein et al. | |
| 5,891,176 A * | 4/1999 | Bornzin ........................... | 607/18 |
| 6,522,923 B1 | 2/2003 | Turcott | |
| 6,792,310 B1 * | 9/2004 | Turcott et al. ................... | 607/27 |
| 6,882,883 B2 | 4/2005 | Condie et al. | |
| 6,978,182 B2 | 12/2005 | Mazar et al. | |
| 7,110,818 B2 | 9/2006 | Anderson et al. | |
| 7,184,835 B2 | 2/2007 | Kramer et al. | |
| 7,200,435 B2 | 4/2007 | Ricci et al. | |
| 7,231,248 B2 | 6/2007 | Kramer et al. | |
| 7,542,803 B2 | 6/2009 | Heruth et al. | |
| 2003/0097158 A1 * | 5/2003 | Belalcazar ...................... | 607/32 |
| 2004/0098065 A1 | 5/2004 | Hagglof et al. | |
| 2004/0106960 A1 | 6/2004 | Siejko et al. | |
| 2005/0038477 A1 * | 2/2005 | Kramer et al. .................... | 607/9 |

(Continued)

FOREIGN PATENT DOCUMENTS

| | | |
|---|---|---|
| EP | 1350539 A1 | 10/2003 |
| EP | 1484083 A1 | 12/2004 |

(Continued)

OTHER PUBLICATIONS

"International Aplication Serial No. PCT/US2007/026191 International Search Report Mailed on May 28, 2008", 7 Pages.

(Continued)

*Primary Examiner* — Carl H Layno
*Assistant Examiner* — Jennifer Ghand
(74) *Attorney, Agent, or Firm* — Schwegman, Lundberg & Woessner, P.A.

(57) ABSTRACT

An implantable cardiac function management device including a programmable controller can be used to include a user-specifiable therapy control parameter set. The therapy control parameter set may then be configured to include at least one therapy control parameter that is user-configurable to automatically switch from a first parameter value to a second parameter value at a time that occurs between separate user programming sessions of the device. Various attributes of physiological measures may allow for refinement of the parameter sets to adapt to changed conditions of the subject. Methods of use are also presented.

20 Claims, 6 Drawing Sheets

(56) References Cited

U.S. PATENT DOCUMENTS

| | | | |
|---|---|---|---|
| 2005/0043767 A1 | 2/2005 | Belalcazar | |
| 2005/0102002 A1* | 5/2005 | Salo et al. | 607/17 |
| 2005/0131469 A1* | 6/2005 | Cohen | 607/9 |
| 2005/0209511 A1* | 9/2005 | Heruth et al. | 600/301 |
| 2005/0216064 A1* | 9/2005 | Heruth et al. | 607/3 |
| 2006/0025830 A1 | 2/2006 | Freeberg | |
| 2006/0106433 A1 | 5/2006 | Mazar et al. | |
| 2006/0111751 A1 | 5/2006 | Cazares | |
| 2007/0135854 A1 | 6/2007 | Kramer et al. | |
| 2007/0156187 A1 | 7/2007 | Ricci et al. | |
| 2007/0162080 A1 | 7/2007 | Brockway et al. | |
| 2009/0254139 A1* | 10/2009 | Bjorling | 607/17 |

FOREIGN PATENT DOCUMENTS

| | | |
|---|---|---|
| EP | 1849412 B1 | 3/2009 |
| WO | WO-03037428 A2 | 5/2003 |
| WO | WO-2005122902 A1 | 12/2005 |
| WO | WO-2008079347 A1 | 7/2008 |

OTHER PUBLICATIONS

"International Aplication Serial No. PCT/US2007/026191 International Written Opinion Mailed on May 28, 2008", 3 pages.

U.S. Appl. No. 12/249,856, Response filed Apr. 13, 2012 to Non Final Office Action mailed Jan. 19, 2012, 11 pgs.

U.S. Appl. No. 12/249,856, Response filed Oct. 17, 2012 to Final Office Action mailed Aug. 17, 2012, 10 pgs.

U.S. Appl. No. 12/249,856, Advisory Action mailed Dec. 18, 2013, 3 pgs.

U.S. Appl. No. 12/249,856, Examiner Interview Summary mailed Oct. 17, 2012, 3 pgs.

U.S. Appl. No. 12/249,856, Final Office Action mailed Aug. 17, 2012, 13 pgs.

U.S. Appl. No. 12/249,856, Final Office Action mailed Oct. 18, 2013, 13 pgs.

U.S. Appl. No. 12/249,856, Non Final Office Action Mailed Jan. 19, 2012, 11 pgs.

U.S. Appl. No. 12/249,856, Non Final Office Action mailed Jun. 17, 2013, 13 pgs.

U.S. Appl. No. 12/249,856, Notice of Allowance mailed Feb. 19, 2014, 7 pgs.

U.S. Appl. No. 12/249,856, Response filed Jan. 20, 2014 to Final Office Action mailed Oct. 18, 2013, 10 pgs.

U.S. Appl. No. 12/249,856, Response filed U.S. Appl. No. 12/249,856, to Final Office Action mailed Oct. 18, 2013, 10 pgs.

U.S. Appl. No. 12/249,856, Response filed Aug. 28, 2013 to Non Final Office Action mailed Jun. 17, 2013, 10 pgs.

* cited by examiner

METHOD AND APPARATUS TO IMPLEMENT MULTIPLE PARAMETER SETS IN AN IMPLANTABLE DEVICE

TECHNICAL FIELD

This document relates generally to cardiac rhythm management (CRM) systems and particularly, but not by way of limitation, to cardiac rhythm management systems and methods that use multiple programmed parameter sets for a patient's implantable stimulation device.

BACKGROUND

In a normal heart, the sinoatrial node, the heart's predominant natural pacemaker, generates electrical impulses, called action potentials, that propagate through an electrical conduction system to the atria and then to the ventricles of the heart to excite the myocardial tissues. The atria and ventricles contract in the normal atrio-ventricular sequence and synchrony to result in efficient blood-pumping functions indicated by a normal hemodynamic performance. These intrinsic action potentials can be sensed on a surface electrocardiogram (i.e., a "surface ECG signal") obtained from electrodes placed on the patient's skin, or from electrodes implanted within the patient's body (i.e., an "electrogram signal"). The surface ECG and electrogram waveforms, for example, include artifacts associated with atrial depolarizations ("P-waves") and those associated with ventricular depolarizations ("QRS complexes").

When people have irregular cardiac rhythms, referred to as cardiac arrhythmias, or poor spatial coordination of heart contractions, diminished blood circulation may result. For such persons, cardiac rhythm management (CRM) systems may be used to improve these conditions. CRM systems include, among other things, pacemakers which deliver timed sequences of low energy electrical stimuli, called pace pulses, to the heart. By properly timing the delivery of pace pulses, the heart can be induced to contract in proper rhythm, improving efficiency. Another type of CRM systems include defibrillators that are capable of delivering higher energy electrical stimuli to the heart. Such defibrillators include cardioverters, which synchronize the delivery of such stimuli to sensed intrinsic heart activity signals. Defibrillators are often used to treat patients with tachyarrhythmias, which can be thought of as abnormal heart rhythms characterized by a rapid heart rate. Fibrillation is a form of tachyarrhythmia further characterized by an irregular heart rhythm.

Upon implantation, a CRM device is programmed to perform in response to detected electrical or mechanical disturbances within the heart. How the device is programmed may have a direct impact upon patient outcome. When the device is first implanted, a caregiver may rely upon historical data to determine how to set the programming parameters to be used until the next follow-up appointment, during which time results may be measured and recorded. After a specified period of time, the patient returns for a follow-up visit with the caregiver, the results are evaluated, and the device is re-programmed, if appropriate.

OVERVIEW

The present inventors have recognized that the iterative nature of the programming process, coupled with the large number of variables which may impact the functionality of the heart may delay finding an improved or optimized programmed parameter set. For these and other reasons, the present inventors have recognized a need for improved techniques of programming parameter sets.

This document describes, among other things, an implantable cardiac function management device including a programmable controller can be used to include a user-specifiable therapy control parameter set. The therapy control parameter set may then be configured to include at least one therapy control parameter that is user-configurable to automatically switch from a first parameter value to a second parameter value at a time that occurs between separate user programming sessions of the device. Various attributes of physiological measures may allow for refinement of the parameter sets to adapt to changed conditions of the subject. Methods of use are also presented.

Example 1 describes an apparatus comprising an implantable cardiac function management device. The implantable cardiac function management device includes a programmable controller. The programmable controller is configured to include a user-specifiable therapy control parameter set. The therapy control parameter set is configured to include at least one therapy control parameter that is user-configurable to automatically switch from a first parameter value to a second parameter value at a time that occurs between separate user programming sessions of the device.

In Example 2, the apparatus of Example 1 is optionally configured to obtain at least one physiological measure for each combination of parameter values of the therapy control parameter set.

In Example 3, the apparatus of at least one of Examples 1 or 2 is optionally configured such that at least one physiological measure includes information from a separate and unattached physiological sensor.

In Example 4, the apparatus of at least one of Examples 1-3 optionally includes the controller configured to determine which combination of parameter values contributed to a particular outcome as evidenced by at least one physiological measure.

In Example 5, the apparatus of at least one of Examples 1-4 optionally includes the controller configured to determine which of the first and second parameter value contributed more to the at least one physiological measure.

In Example 6, the apparatus of at least one of Examples 1-5 optionally includes the controller configured to suggest at least one combination of parameter values as a function of past physiological measures.

In Example 7, the apparatus of at least one of Examples 1-6 optionally includes the device having multiple therapy control parameter sets, wherein the device is configured to sequence through two or more of the therapy control parameter sets.

In Example 8, the apparatus of at least one of Examples 1-7 is optionally configured with at least one therapy control parameter set that includes at least one of a user-configurable range and a user-configurable duration.

In Example 9, the apparatus of at least one of Examples 1-8 is optionally configured such that the sequence occurs symmetrically from an initial parameter set to a final parameter set.

In Example 10, the apparatus of at least one of Examples 1-9 is optionally configured such that the duration is user-specifiable as a period of time.

In Example 11, the apparatus of at least one of Examples 1-10 is optionally configured such that the duration is user-specifiable as expiring upon reaching a threshold of detected events.

Example 12 includes a method comprising receiving user input to program a cardiac function management device and using the user input to automatically alter, at a time that occurs between separate user-programming sessions, a parameter value of at least one therapy control parameter.

In Example 13, the method of Example 12 is optionally performed such that it includes obtaining at least one physiological measure for each combination of parameter values of the therapy control parameter set.

In Example 14, the method of at least one of Examples 12-13 optionally includes determining which of the combination of parameter values contributed to a particular outcome as evidenced by at least one physiological measure.

In Example 15, the method of at least one of Examples 12-14 optionally includes using the user input for automatically sequencing through multiple therapy control parameter sets at times occurring between separate user-programming sessions.

In Example 16, the method of at least one of Examples 12-15 optionally includes using at least one of a user-specified range and a user-specified duration for performing the sequencing.

In Example 17, the method of at least one of Examples 12-16 optionally includes using a user-specified duration that is user-specified as a time.

In Example 18, the method of at least one of Examples 12-17 optionally includes using a user-specified duration that is user-specified as a threshold number of detected events.

In Example 19, the method of at least one of Examples 12-18 is optionally performed such that the sequencing occurs sequentially from the initial parameter set to the final parameter set.

Example 20 describes an apparatus comprising means for receiving user input to program a cardiac function management device and means for using the user input to automatically alter, at a time that occurs between separate user-programming sessions, a parameter value of at least one therapy control parameter.

In Example 21, the apparatus of Example 20 is optionally configured such that it includes means for obtaining at least one physiological measure for each combination of parameter values of the therapy control parameter set.

In Example 22, the apparatus of at least one of Examples 20-21 optionally includes means for automatically sequencing, using the user input, through multiple therapy control parameter sets at times occurring between separate user-programming sessions.

In Example 23, the apparatus of at least one of Examples 20-22 optionally includes means for using at least one of a user-specified range and a user-specified duration for performing the sequencing.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
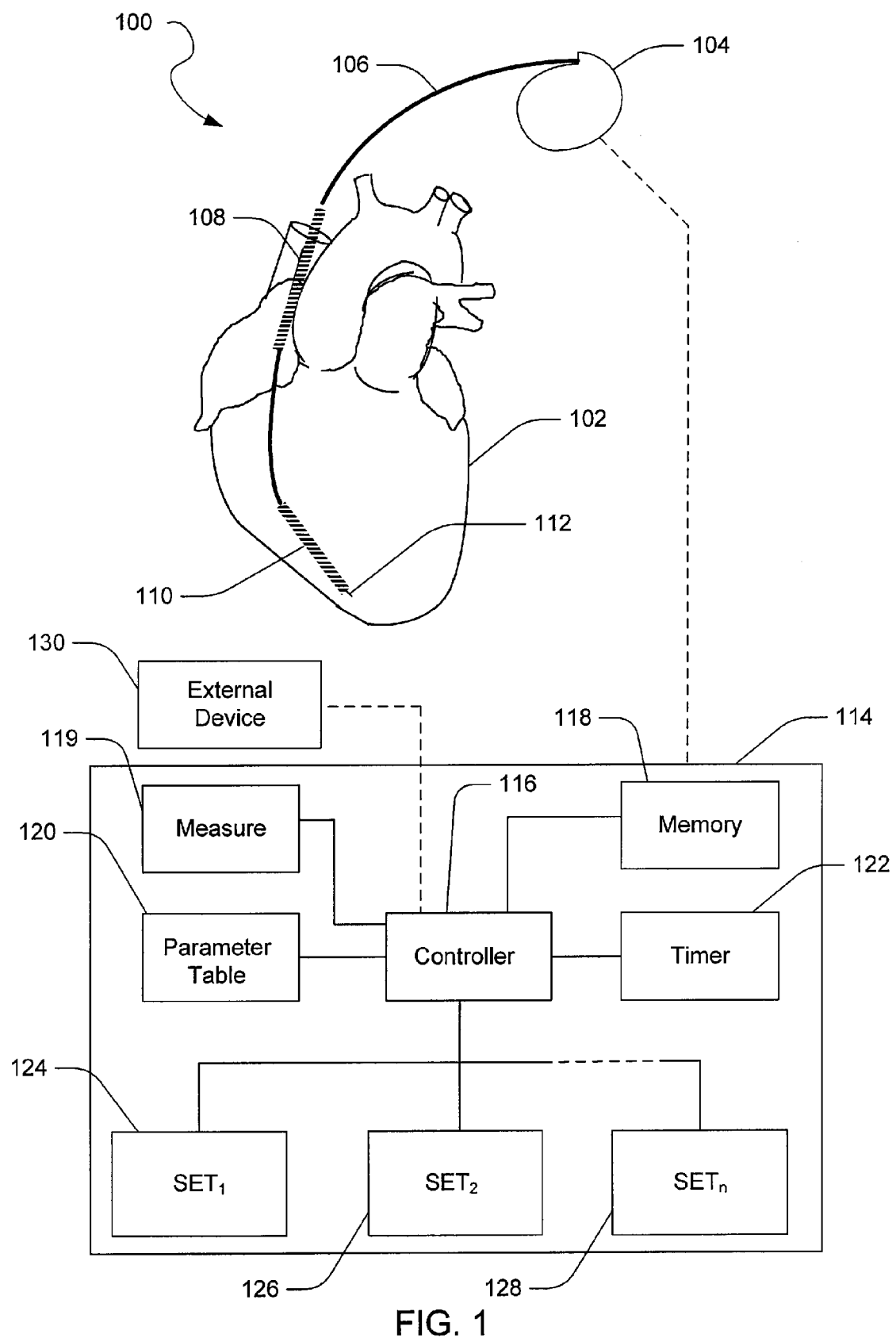
FIG. 1 illustrates an example of portions of a system which utilizes a device for monitoring and controlling electrical signals of the heart.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The present systems and methods are described with respect to implantable medical devices such as neurostimulation devices, gastrointestinal stimulation devices, retinal implants, cochlear implants and including CRM devices, such as pacemakers, cardiac function management devices (CFMDs), implantable cardioverter-defibrillators (ICDs), pacer-defibrillators, and single or multi-chamber cardiac resynchronization therapy (CRT) devices that use pacing. The device may also be programmed to monitor and store one or more measured physiological parameters using a given programmed parameter set. In certain examples, the programmed parameter set contains a single parameter adjusted among one or more values within a specified range. In another example, the programmed parameter set comprises multiple parameters adjusted among one or more values within a specified range. In certain examples, the programmed parameter set is determined as a function of one or more measured physiological parameters such as by use of an algorithm to calculate a value for use in at least one programmed parameter set. In certain examples, the device may identify safe limits such that an adverse condition would prompt a stop condition for at least one parameter set. The monitored or stored information may indicate information about the patient's response to a given parameter set and thereby can sometimes be used to determine an improved programmed parameter set. For example, one measured physiological parameter may indicate how the heart reacts during one or more specific activities that, when repeated, can identify a value for a programmed parameter set or determinable condition or outcome. In another example, a "target" physiological outcome may be specified, and the stored physiological information corresponding to a particular programmed parameter set may be compared against this target such as to determine whether any changes should be made to the programmed parameter set.

Each programmable parameter set may fit as part of a larger optimization program which uses ranges of parameter settings (e.g., AV delay range) and durations of each parameter set occurring in time (e.g., period of forty-eight hours). One example of this type of organization of variables uses a design of experiments (DOE). In DOE, a model, or series of models, can be developed to help determine what variables (e.g., parameter sets) affect a response of interest (e.g., % AV pacing). Using this method, one can determine certain variables, and can separate any dependent variables, which change in response to a change in one or more other variables, from any independent variables, which do not change in response to a change in one or more other variables. When only a few variables exist, the analysis may not need formal DOE, however, it is useful for a large number of variables or a complex interaction between variables. In certain examples, the automatic variation in one or more parameters, coupled with automatic analysis of one or more corresponding results obtained for different values of the one or more parameter, can be used to select (or to help a caregiver select) a set of parameter values that will produce a high probability of a desired response. This can reduce or eliminate clinician guess work and can obtain useful information about the effect of designed variations of one or more parameter values during the period of time between the implant of a device and the next patient follow-up, or between follow-ups. This can save time and allow much more information to be presented to the caregiver for tailoring the device for the patient.

Moreover, post-implant DOE techniques can provide data that will enable both caregivers and device manufacturers to explore performance variations resulting from parameter value variations. This information can be used to improve desirable patient outcomes earlier in the life of a particular model of device, for example. In certain examples, implanting a CRM device may involve programming a set of default parameter values based upon historical information about the subject's physiological condition before implantation. One or more parameter values can be controllably varied, and one or more specified indicators can then be monitored until the next follow-up between the caregiver and the subject. At that point, any recorded results may be reviewed by the caregiver, who may decide to modify one or more device parameter values, or automatically evaluated by the implanted device itself or by an ancillary external device. This may provide an early indication of the subject's response to a given therapy. Considering that a single programmed parameter set over the period of time (e.g., six months) provides a limited amount of information about the subject's response, the ability to provide multiple parameter sets occurring sequentially, or in combination, may provide significantly more valuable data for the caregiver or the device to evaluate.

FIG. 1 illustrates portions of a system 100 that uses a device 104 (e.g., implantable cardiac function management device), such as for monitoring one or more electrical signals of the heart 102. In certain examples, the device 104 may be coupled to one or more lead wires 106 having a first coil electrode 108, a second coil electrode 110, and a tip electrode 112, however, a leadless implementation is also possible. An electrogram signal (EGM) may be detected from one or more intrinsic electrical signals occurring within the heart 102, thereby providing information about heart contractions, such as an indication of heart rate, and information about how the values of the control parameters of the device 104 affect the rate. In this example, a control module 114 includes a programmable controller 116, which may be capable of performing several functions. In certain examples, programmable controller 116 may select a user-specifiable therapy control parameter value from a parameter table 120 as a result of receiving input from a user or caregiver. The parameter table 120 may contain a listing of one or more adjustable parameters, each having specified candidate values and a duration within which each such candidate value is to be applied. A specified range of a given control parameter may limit the candidate values of a particular parameter, such as by specifying a minimum value or maximum value.

For example, one possible therapy control parameter may include an atrioventricular (AV) delay that may have a specified range of possible candidate AV delay times that may be selected for a given parameter set. The AV delay may be associated with one or more parameter sets 124, 126 and 128. Each parameter set may include one or more user-specifiable therapy control parameters having a user-configurable range (or other specification of candidate values) and a user-configurable duration. For example, the duration of a specified candidate control parameter, within a particular parameter set, may include an associated period of time, such as forty eight hours, during which time a selected AV delay candidate value will be applied as part of a specified parameter set (e.g., 124, 126 or 128). A timer 122 may be used to count the duration for using a given parameter value or for using an entire parameter set (e.g., 124, 126 or 128). In certain examples, a parameter value will automatically switch from one value to another between parameter sets, such as to perform a DOE style variation in parameter values using the different parameter sets. In certain examples, the user-configurable duration may expire upon the measure module 119 reaching a threshold value. In certain examples, the device 104 cycles through various different parameter sets (e.g., 124, 126 or 128), such as during the period of time between an implant of the device 104 and a remote or local follow-up between a caregiver and the subject.

In the example of FIG. 1, an initial or first parameter set 124 ($SET_1$), may represent a first set of user-specified values and corresponding durations of specified device control or operating parameters from the parameter table 120. For example, the first parameter set 124 may list an AV delay parameter with a parameter value of 5 ms to be applied for a duration of forty-eight hours from a start to an end of a period during which the first parameter set 124 is in effect. Similarly, a second parameter set 126 ($SET_2$), may represent a second set of specified parameters from the parameter table 120. In certain examples the second parameter set 126, may be automatically put into effect upon the completion of a duration of the first parameter set 124 or of one or more durations of one or more specified therapy control parameters within a first parameter set 124. In yet another example, the second parameter set 126 may be automatically activated before the completion of the duration of the first parameter set 124, for example, upon measuring a response that meets a particular threshold value. The second parameter set 126 may automatically alter at least one parameter value from the first parameter set 124. A final parameter set 128 ($SET_N$), may represent the last parameter set among a number of specified parameter sets.

During the application of the various parameter sets, there may be one or more physiological measures collected by the measure module 119 to be stored within memory 118. The programmable controller 116 may obtain information about the one or more physiological measures in association with a combination of control parameter values in effect during a timer period when the physiological measure was obtained. Examples of one or more physiological measures to be monitored include but are not limited to heart rate, blood pressure, percent atrial or ventricular pacing, etc. A separate and unattached implantable or external physiological sensor may be used to obtain one or more physiological measures. Additionally, external device 130 may provide a physiological measure—and may interact with or operate independently of the programmed parameter sets. In certain examples, the external device 130 may include a weight scale, a blood pressure cuff, etc.

Figure 2:
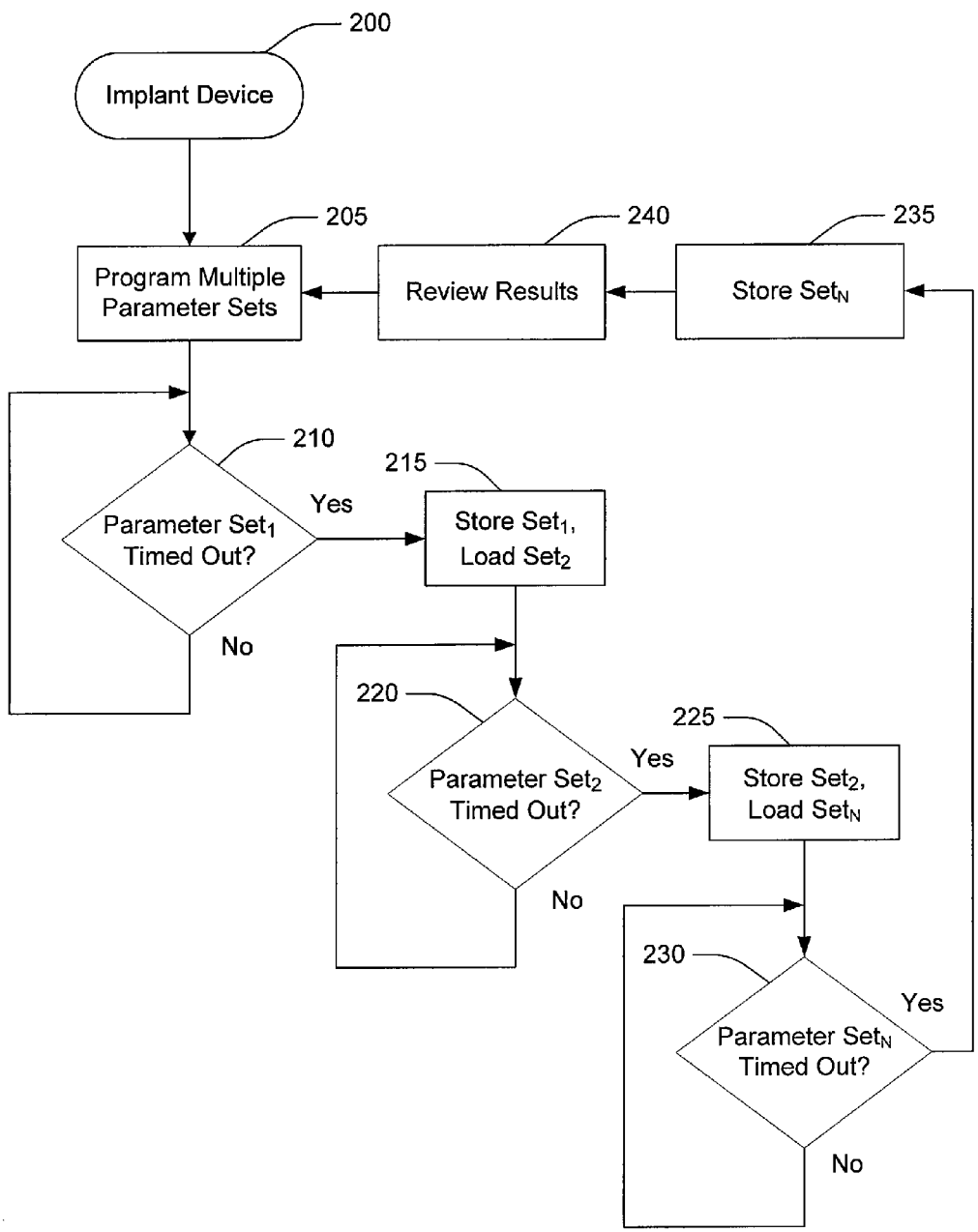
FIG. 2 is a flow chart illustrating generally an example of portions of a technique for programming multiple parameter sets and storing responses.

FIG. 2 is a flow chart illustrating generally an example of portions of a technique for programming multiple parameter sets and storing responses. In certain examples, the start of a programming cycle (or beginning of a first parameter set) follows the implant of an ICD or other implantable medical device. At 200, a device may be implanted within the body of a subject for monitoring intrinsic cardiac signals and, at 205, a control module (similar to control module 114 of FIG. 1) may be programmed with more than one parameter set ($SET_1$, ..., $SET_N$). In certain examples, a program may specify a first set of parameter values for first parameter set $SET_1$ and an associated duration. During at least a portion of the duration of the first parameter set $SET_1$, one or more physiological measures may be monitored and recorded.

At 210, the first parameter set $SET_1$ may be monitored for completion of its specified duration. If the duration has not yet reached completion, the control module 114 will continue to monitor. If however, at 210, duration of the first parameter set $SET_1$ has reached completion, at 215, the monitored potential outcome variables may be stored and associated with first parameter set $SET_1$ for later reference or retrieval. Additionally, at 215, the second parameter set $SET_2$ may be loaded by the control module 114 to begin the next phase of the programming cycle. In certain examples, the control module 114 may be programmed to delay the start of a subsequent parameter set for a specified duration, such as to establish a steady-state or reference condition before activating the next parameter set. In certain examples, this may involve returning to an interim parameter set between successive trial parameter sets. At 220, the second parameter set ($SET_2$) may be monitored for completion of its specified duration. Until its duration reaches completion, the control module 114 will continue to monitor and may record one or more specified outcome variables. Upon completion of the duration, at 225, the monitored potential outcome variables may be stored and associated with the second parameter set $SET_2$ for later reference or retrieval. At 215, the final parameter set $SET_N$ may be loaded by the control module 114 to begin the final phase of the programming cycle. At 230, duration of the final parameter set $SET_N$ is monitored by the control module 114 until completion of its duration. Upon completion of its duration, at 235, the monitored potential outcome variables may be stored. At 240, the caregiver may review the results associated with one or more parameter sets ($SET_1$, ..., $SET_N$). The caregiver may then use this information to choose, at 205, a parameter set for subsequent operation, or to create another DOE of multiple parameter sets to be executed before another follow-up.

Figure 3:
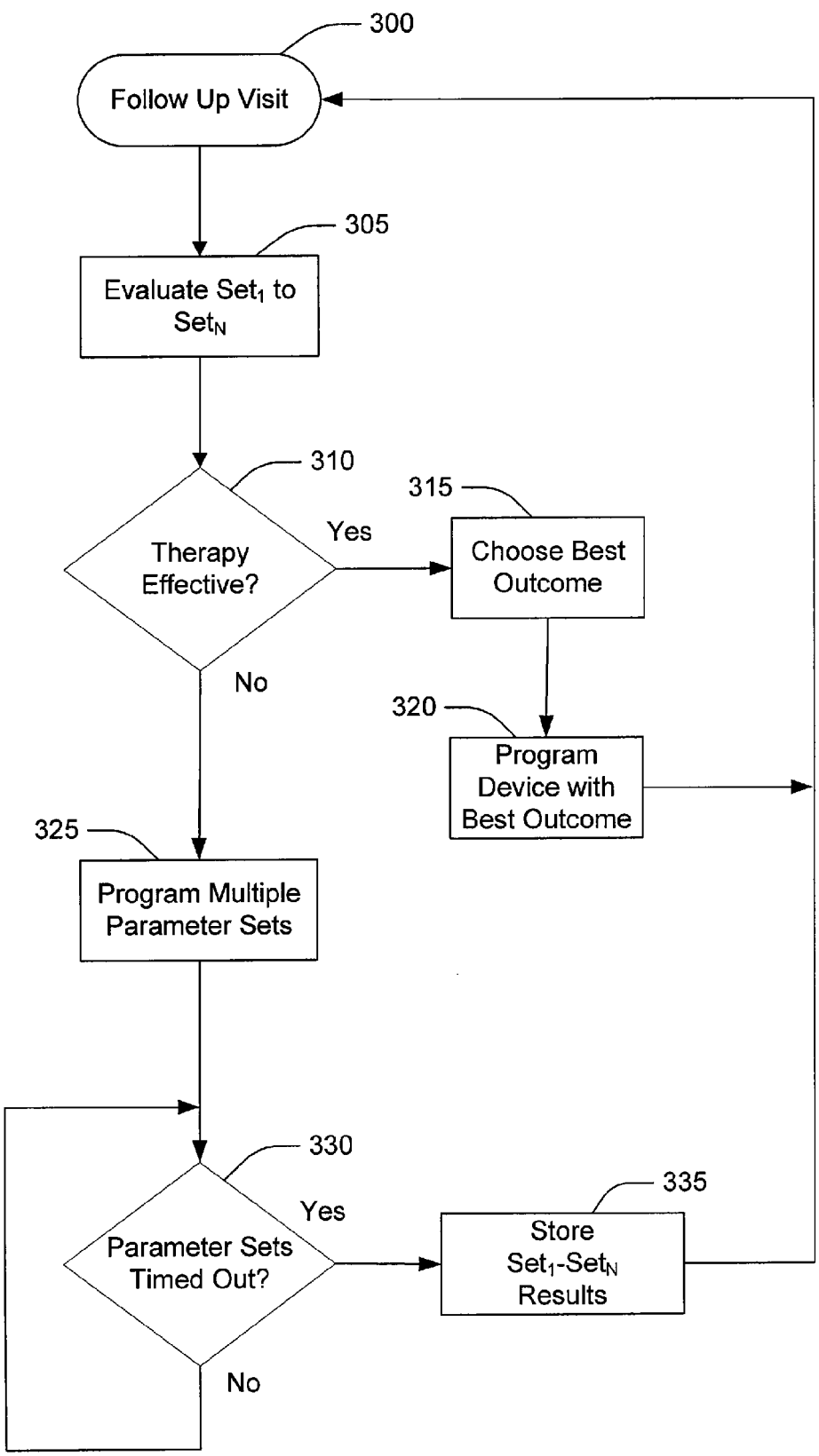
FIG. 3 is a flow chart illustrating generally an example of how the results of the multiple parameter sets are evaluated and revised, such as for optimization.

FIG. 3 is a flow chart illustrating generally an example of how the monitored results of the multiple parameter sets can be evaluated and parameter values improved or optimized, such as that performed at 240 of FIG. 2. At 300, a follow-up may be scheduled to review the results obtained from the one or more parameter sets ($SET_1$, ..., $SET_N$). At 305, the stored results may be evaluated to determine if a change in one or more programmed parameter values is warranted, or if further monitoring of results for different parameter sets is warranted. The caregiver may choose to have the information presented in a trended or other graphical representation to better represent the connection between a particular parameter set (or chosen therapy) and a corresponding monitored physiological measure. At 310, the caregiver may make a determination as to the effectiveness of the applied therapy (associated with the corresponding parameter sets). The therapy may be deemed effective if one or more parameter sets caused a desired outcome in one or more monitored physiological measures. If the caregiver determines that the therapy was effective (e.g., best outcome reached), at 315, the identified one or more control parameter values are chosen from the one or more parameter sets ($SET_1$-$SET_N$) and at 320, the control module 114 may be programmed to use the chosen parameter values for a subsequent specified duration or indefinitely, during which time the control module 114 may continue to monitor one or more physiological measures, if the user desires. Upon completion of the best outcome duration, at 300, a follow-up may occur.

If, at 310, the caregiver determines that the therapy was not effective, then at 325, one or more programmed parameter sets can be revised, such as for further experimentation and monitoring. At 330, the one or more parameter sets ($SET_1$, ..., $SET_N$) are monitored until their durations have completed, thereafter, at 335, the results associated with physiological measures are stored. At 300 a follow up is carried out.

Figure 4:
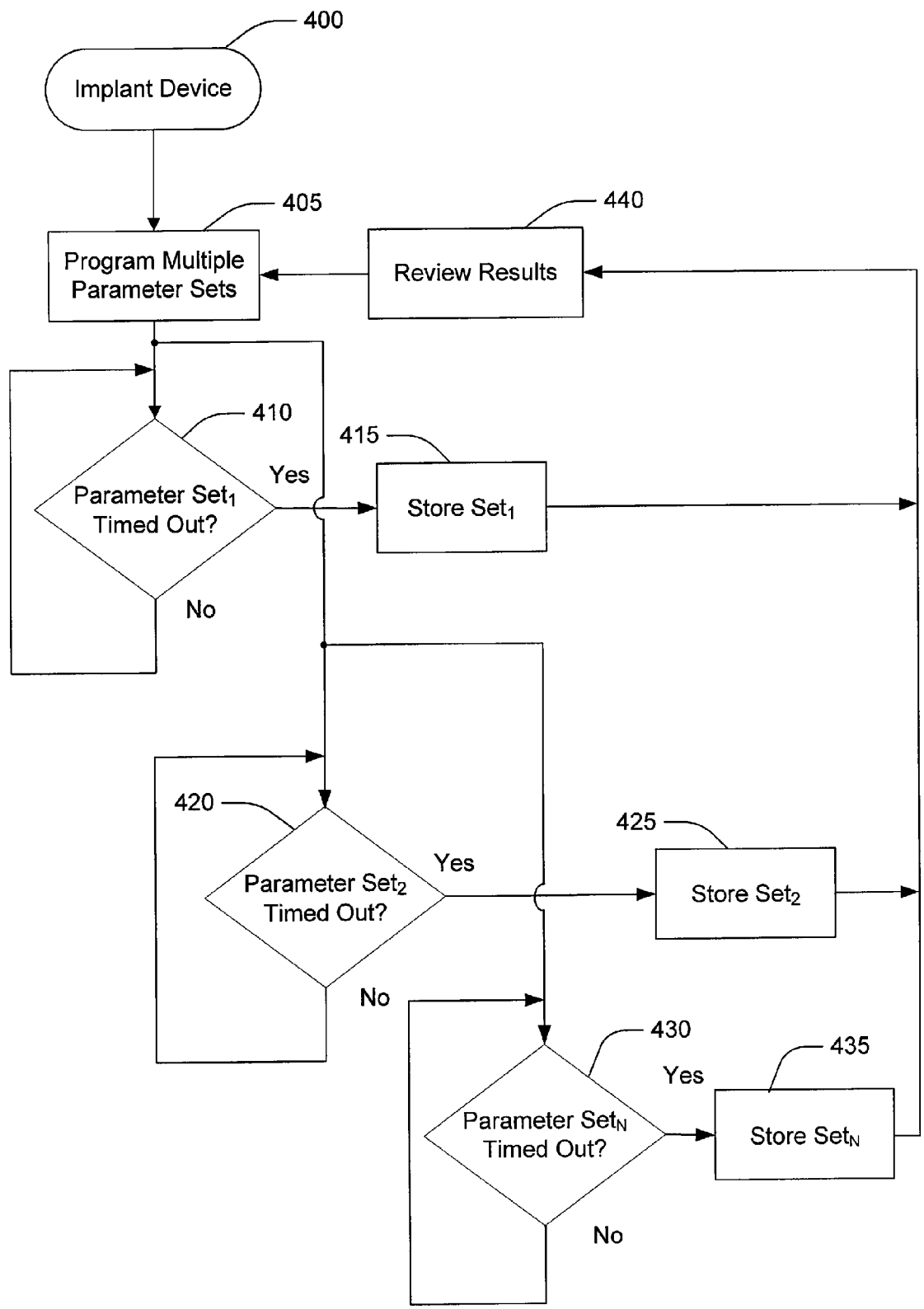
FIG. 4 is a flow chart illustrating generally an example of how multiple parameter sets may operate concurrently.

DOE permits understanding of the effect that each variable has on a given system. As a result, multiple parameters may be concurrently varied in value, and DOE techniques used to extract the impact of a particular parameter on the resulting monitored physiological output variable. FIG. 4 is a flow chart illustrating generally an example of how multiple parameter sets may operate concurrently. At 400, a device may be implanted within the body of a subject for monitoring intrinsic cardiac signals. At 405, a control module 114 (similar to control module 114 of FIG. 1) may be programmed with more than one parameter set ($SET_1$, ..., $SET_N$). In certain examples, one or more parameter sets such as first parameter set $SET_1$ 410, second parameter set $SET_2$ 420 and final parameter set $SET_N$ 430 may occur concurrently or be subject to overlap of varying durations. The control module 114 may monitor physiological measures for each parameter set in combination or separately until each has completed its duration. Upon completion of the duration of the first parameter set $SET_1$ 410, second parameter set $SET_2$ 420 and final parameter set $SET_N$ 430, the control module 114 will store the monitored results at 415 ($SET_1$), 425 ($SET_2$) and 435 ($SET_N$), respectively. At 440, all of the results are reviewed by the caregiver at the next follow-up visit with the subject.

Figure 5:
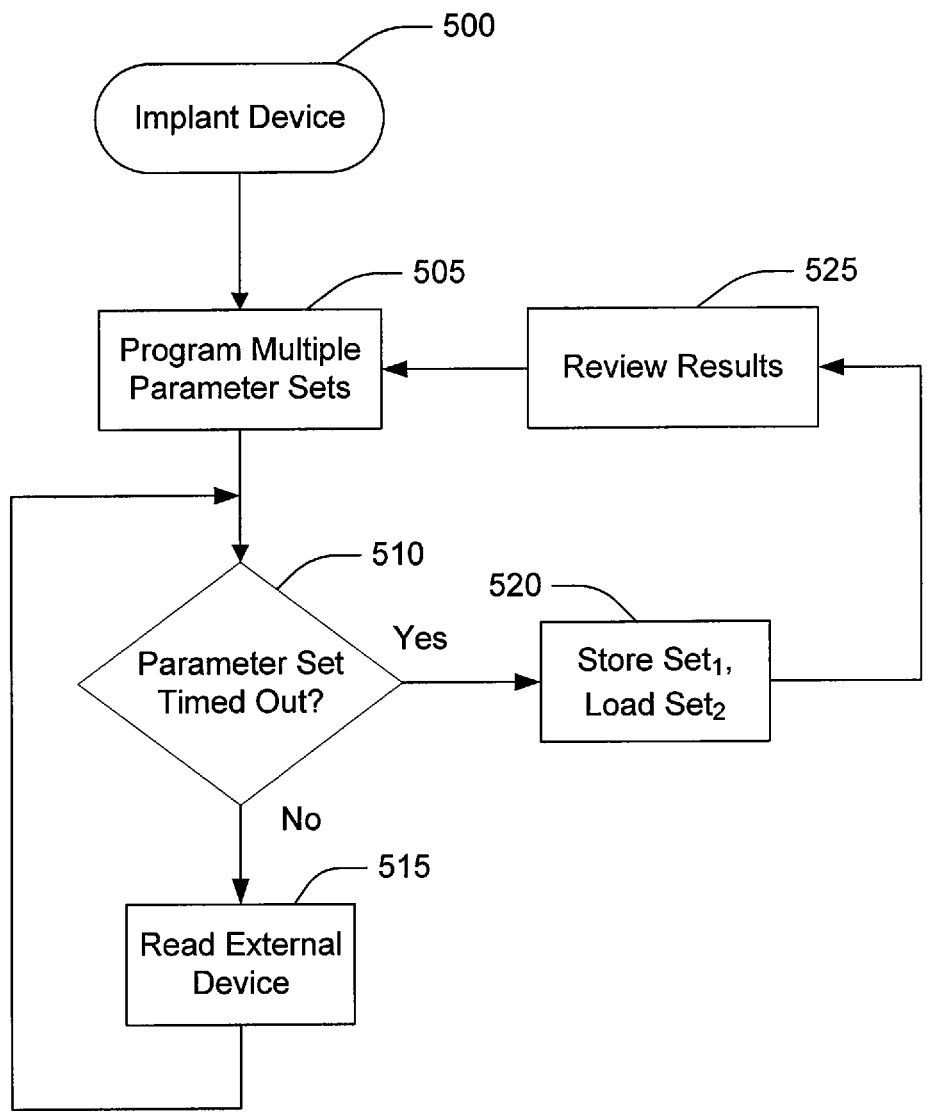
FIG. 5 is a flow chart, similar to FIG. 2, but illustrating an example of a technique in which an external device parameter is read as part of the programmed parameters.

In certain examples, the control module 114 may collect information from an external device 130 to be used as part of the therapy for the subject and as a variable to be analyzed with the implantable cardiac rhythm management device and related specified parameter sets. In FIG. 5, the caregiver may implant an implantable cardiac rhythm management device at 500 and, at 505, one or more programmable parameter sets may be programmed with a one or more parameters having a range or varying values and a duration. At 510, the control module 114 waits for the parameter set's duration to elapse. In certain examples, the control module 114 recurrently or periodically checks for a completed duration and initiates a read operation to obtain updated information from the external device 515, e.g., just before such completion. At 520, the duration of one or more parameter sets has reached completion, and the monitored physiological measures may be stored and associated with the particular parameter set for future reference or retrieval. At 520, any remaining parameter sets may be loaded by the control module 114 to begin the next phase of the programming cycle. At 525, the results may be reviewed by a caregiver at a follow-up, such as before repeating a new cycle of parameter sets.

In certain examples, a caregiver may indicate a desired outcome or target value for a particular physiological measure, in anticipation of reaching the target value during implementation of one or more control parameters or among one or more parameter sets. In certain examples, one or more quantitative criteria based upon one or more monitored physiological parameters may prompt the control module 114 to select one or more parameter sets. For example, a system 100 may include one or more sensors to measure right and left ventricular pressure and a target value that can be specified by a user or caregiver. In certain examples, this target value may represent an increase in ventricular pressure over time (dP/dt), an increase in stroke volume, or a decrease in mechanical dyssynchrony. In such examples, the control module 114 may determine which parameter set resulted in reaching the target value and may further select a next parameter set based upon this determination. In such cases, there may be a need to store a target result within the control module 114 and later compare a monitored result to the target value. The target may be representative of one or a combination of multiple physiological measures. Similarly, the control module 114 may be configured to identify which parameter set produces a target result and to store that information. For example, this may include identifying and storing the parameter set associated with the largest increase in ventricular pressure or a largest decrease in mechanical dyssynchrony.

Figure 6:
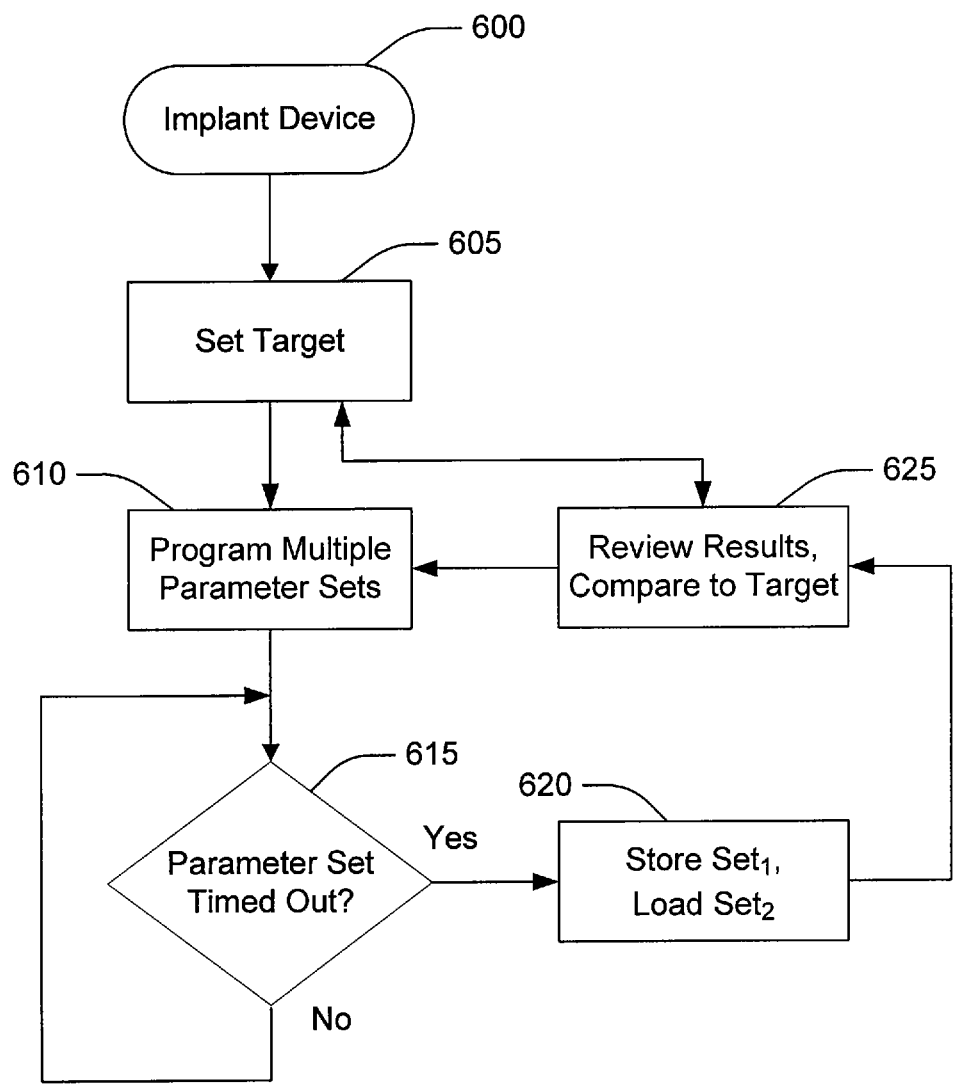
FIG. 6 is a flow chart of an example, similar to FIG. 2, in which the implantable cardiac function management device includes a target outcome which is later compared against the results.

In FIG. 6, at 600, the caregiver implants an implantable cardiac device within the body of a subject. At 605, the caregiver specifies a target value for one or more physiological measures. At 610, the control module 114 may be programmed with one or more parameter sets, as discussed above. At 615, one or more physiological quantities corresponding to a parameter set may be monitored by the control module 114 until a completed duration is reached. At such time, at 620, the monitored results may be stored by the control module 114. Then, at 625, the results of at least one parameter set associated with past physiological measures may be reviewed and compared against the one or more targets at 605. At 610, the next parameter set may be loaded, or alternatively, based upon the comparison of the results from the prior parameter set, a modified parameter set may be programmed by the control module 114 to run next. In this manner, the caregiver may have a specified range within which the program may operate and refine a parameter set with the goal of reaching a specified target without additional follow-ups. Alternatively, a proposed set of parameter settings may be suggested at 610, to be reviewed by the caregiver at the next follow-up. In certain examples, the device may use one or more search techniques to explore measured physiological parameters and improve or optimize a programmed parameter set. For example search techniques may include, but are not limited to hill climbing, genetic search, heuristic search, A* ("A star" search, simulated annealing, or min-max.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. An apparatus comprising:
  an implantable cardiac function management device including a programmable controller, the programmable controller configured to include at least first and second user-specifiable therapy control parameter sets, wherein each of the first and second therapy control parameter sets include:
    a plurality of user-specifiable control parameters including a first control parameter that interacts with a second control parameter; and
    at least one therapy control parameter that is user-configurable to automatically switch from a first parameter value to a second parameter value at a time that occurs between separate user programming sessions of the device;
  wherein the first therapy control parameter set operates during at least a first time duration and the second therapy control parameter set operates during at least a second time duration, and wherein the device is configured to monitor a physiological measure in response to the first therapy control parameter set and compare the physiological measure with a target value for the physiological measure, the device being configured to modify the second therapy control parameter set, prior to the device implementing the second therapy control parameter set, based upon:
    the comparison between the physiological measure and the target value for the physiological measure; and
    a comparison of at least one parameter of the second therapy control parameter set to a user-specified range for that parameter;
  wherein the controller is configured to concurrently vary multiple therapy control parameters and determine an impact of a particular individual therapy control parameter on the resulting monitored physiological measure.

2. The apparatus of claim 1, wherein the controller is configured to obtain at least one physiological measure for each combination of parameter values of the therapy control parameter set.

3. The apparatus of claim 2, wherein the at least one physiological measure includes information from a separate and unattached physiological sensor.

4. The apparatus of claim 2, wherein the controller is configured to determine which combination of parameter values contributed to a particular outcome as evidenced by at least one physiological measure.

5. The apparatus of claim 4, wherein the controller is configured to determine which of the first and second parameter value contributed more to the at least one physiological measure.

6. The apparatus of claim 4, wherein the controller is configured to suggest at least one combination of parameter values as a function of past physiological measures.

7. The apparatus of claim 1, wherein the device includes multiple therapy control parameter sets, and wherein the device is configured to sequence through two or more of the therapy control parameter sets.

8. The apparatus of claim 7, wherein at least one therapy control parameter set includes at least one of a user-configurable range and a user-configurable duration.

9. The apparatus of claim 7, wherein the device is configured to sequence from an initial parameter set to a final parameter set while using each parameter set for an equal duration of time.

10. The apparatus of claim 9, wherein the duration is user-specifiable as a period of time.

11. The apparatus of claim 9, wherein the duration is user-specifiable as expiring upon reaching a threshold of detected events.

12. The apparatus of claim 1, wherein multiple parameters are varied in value during overlapping durations of time.

13. The apparatus of claim 1, wherein the device includes multiple therapy control parameter sets, and wherein the device is configured to operate multiple parameter sets during overlapping durations of time.

14. The device of claim 1, wherein the target value of physiological measure includes a target value of ventricular pressure.

15. The device of claim 1, wherein the target value of physiological measure includes a target value of an increase in ventricular pressure over time (dP/dt).

16. The device of claim 1, wherein the device is configured to modify a therapy control parameter of a next parameter set based upon a comparison of the results of a prior parameter set in achieving the target value.

17. The apparatus of claim 1, wherein the device is configured to determine at least one of the parameter sets according to a desired device outcome.

18. The apparatus of claim 17, wherein the desired device outcome includes a target percentage of atrial-ventricular (AV) pacing.

19. The apparatus of claim 1, wherein the device includes multiple therapy control parameter sets, and wherein the device is configured to delay operation of a second parameter set after operation of a first parameter set has completed.

20. The apparatus of claim 1, wherein the target value comprises a user-specified target value.

* * * * *